(12) United States Patent
Miyamura et al.

(10) Patent No.: US 6,916,920 B2
(45) Date of Patent: Jul. 12, 2005

(54) PROCESS FOR PRODUCING HYDRAZINOMONOSACCHARIDE DERIVATIVES AND USE THEREOF

(75) Inventors: Tsuyoshi Miyamura, Shiga (JP); Tomoe Egashira, Shiga (JP); Mutsumi Sano, Shiga (JP); Brad K. Bendiak, Denver, CO (US); Ikunoshin Kato, Kyoto (JP)

(73) Assignee: Takara Bio Inc., Shiga (JP)

( * ) Notice: Subject to any disclaimer, the term of this patent is extended or adjusted under 35 U.S.C. 154(b) by 99 days.

(21) Appl. No.: 10/343,624

(22) PCT Filed: Jul. 30, 2001

(86) PCT No.: PCT/JP01/06524

§ 371 (c)(1),
(2), (4) Date: Feb. 3, 2003

(87) PCT Pub. No.: WO02/12254

PCT Pub. Date: Feb. 14, 2002

(65) Prior Publication Data

US 2004/0006221 A1 Jan. 8, 2004

(30) Foreign Application Priority Data

Aug. 2, 2000 (JP) ........................................ 2000-234508

(51) Int. Cl.$^7$ .............................. C07H 5/04; C07H 5/06
(52) U.S. Cl. ...................... 536/53; 536/18.7; 536/55.3; 536/123.1; 536/124; 536/17.2; 536/17.9; 536/18.2; 536/18.5
(58) Field of Search ........................ 536/53, 18.7, 55.3, 536/123.1, 124, 17.2, 17.9, 18.2, 18.5

(56) References Cited

U.S. PATENT DOCUMENTS 5,403,927 A 4/1995 Bendiak
5,585,473 A * 12/1996 Bendiak .................... 536/18.7

FOREIGN PATENT DOCUMENTS

EP 649427 A1 4/1995
EP 0 867 722 A2 9/1998
WO WO 91/18912 A1 12/1991

OTHER PUBLICATIONS

Ridley et al. (Analytical Biochemistry (1997) 249, 10–19).*
Lindberg, Bengt, "Methylation Analysis of Polysaccharides", Methods in Enzymology, ed. Victor Ginsburg, Academic Press, New York, 1972, pp. 178–195.
Hase et al, "Reexamination of the Pyridylamination Used For Fluorescence Labeling of Oligosaccharides and its Application to Glycoproteins" J. Biochem. vol. 95, No. 1, 1984, pp. 197–203.
Ridley et al, "A Method for Biotin Lbeling of Viologically Active Oligogalacturonides Using a Chemically Stable Hydrazide Linkage" Analytical Biochemistry, vol. 249, 1997, pp. 10–19.

* cited by examiner

Primary Examiner—James O. Wilson
Assistant Examiner—Michael C. Henry
(74) Attorney, Agent, or Firm—Browdy and Neimark

(57) ABSTRACT

A process for producing hydrazinomonosaccharide derivatives and use of hydrazines in determining the structures of aldose and ketose monosaccharides located at the reducing ends of saccharides.

2 Claims, 1 Drawing Sheet

US 6,916,920 B2

PROCESS FOR PRODUCING HYDRAZINOMONOSACCHARIDE DERIVATIVES AND USE THEREOF

TECHNICAL FIELD

The present invention relates to a method for producing hydrazino monosaccharide derivatives which is useful for analyses of monosaccharides and use thereof. Specifically, the present invention relates to use of hydrazines for the production of hydrazino monosaccharide derivatives and for the determination of structures of aldose or ketose monosaccharides at reducing ends of saccharides.

BACKGROUND ART

Saccharides (also called sugars or carbohydrates) are main components of biological systems. Saccharides constitute about 80% of dry weight of plants and, either as monomers (monosaccharides) or polymers consisting of monosaccharides covalently bound each other (oligosaccharides), are indispensable components of metabolic pathways in higher animals. In addition, saccharides are often found as parts of larger biological macromolecules (including proteins, lipids and nucleic acids). Saccharides in such various forms have numbers of important functions in nature.

A means of identifying a free monosaccharide or a monosaccharide as a monomeric component of an oligosaccharide is very useful because of the importance of saccharides in biological systems. Furthermore, a means of identifying a monosaccharide at a reducing end of an oligosaccharide is important for the structural analysis of the oligosaccharide.

Recently, a method for analyzing a structure of an oligosaccharide was disclosed in WO 96/17824 (JP-A 11-501901). In the method, a monosaccharide at a reducing end of an oligosaccharide is converted to an N,N'-diacetylhydrazino monosaccharide derivative, and the derivative is identified by gas chromatography/mass spectrometry (GC/MS) or the like. Theoretically, the types of monosaccharides at the reducing ends of all oligosaccharides can be identified according to this method.

However, there is a problem that one can use the above-mentioned method only for an isolated saccharide. If this method is applied to a mixture of several kinds of saccharides, it is impossible to determine the saccharides from which the respective resulting several kinds of hydrazino monosaccharides derive. Thus, if a naturally occurring saccharide is to be analyzed according to this method, it is necessary to isolate the saccharide beforehand.

For example, since a protein or a nucleic acid itself has ultraviolet absorbance, it is possible to trace the position during separation/purification procedures based on the absorbance. However, since a saccharide does not have such absorbance, it is desired to label the saccharide in order to facilitate separation/purification. For example, labeling with a fluorescent dye is suitable for this purpose. If a saccharide coexists with other contaminants derived from a natural source (e.g., proteins, nucleic acids, etc.), the saccharide having a label should be readily distinguished from other contaminants. Thus, in this case, a saccharide must be selectively labeled such that contaminating components other than the saccharide are not labeled.

A method for labeling a reducing residue of a saccharide exemplifies a method for selectively labeling a saccharide without labeling other components derived from a natural source. Examples of reducing residues include a carbonyl group at a reducing end of a saccharide and a free aldehyde group. Reactions on reducing residues of saccharides include a reductive amination reaction and a hydrazidation reaction. These reactions are irreversible. A method in which 2-aminopyridine is used (S. Hase, T. Ibuki and T. Ikenaka, Journal of Biochemistry, 95, 197–203 (1984)) exemplifies a method for labeling a saccharide using a reductive amination reaction. A method in which Biotin-x-hydrazide (Calbiochem) is used (B. Ridley, D. Mohnen et al., Analytical Biochemistry, 249, 10–19 (1997)) exemplifies a method for labeling a saccharide using a hydrazidation reaction. In the latter method, a saccharide labeled with biotin through a hydrazide bond is prepared by forming a hydrazone by a reaction of a saccharide having a reducing end with Biotin-x-hydrazide and then conducting a reduction reaction.

A free reducing end of a saccharide is utilized in the method disclosed in WO 96/17824. Therefore, it is impossible to directly use a monosaccharide isolated by labeling a reducing end of a saccharide according to this method for identifying the type thereof.

Furthermore, determination of the position of binding to a neighboring monosaccharide (hereinafter also referred to as the "substitution position") is desired in addition to identification of the type of a monosaccharide in order to precisely determine the structure of a monosaccharide at a reducing end of a saccharide. In other words, it is desired to determine the position of a hydroxyl group of a neighboring monosaccharide through which a monosaccharide at a reducing end binds. Only a technique for identifying the type of a monosaccharide at a reducing end of a saccharide is disclosed in WO 96/17824. A technique for determining the substitution position is not mentioned therein.

A methylation analysis is known as a method for determining the position of binding between monosaccharides constituting a saccharide. A general methylation analysis comprises methylation of an oligosaccharide, hydrolysis of the methylated oligosaccharide, reduction of a free methylated monosaccharide, acetylation of a methylated alditol, and an analysis of a partially methylated alditol acetate (PMAA) in this order. Fragmentation patterns for partially methylated alditol acetates upon mass spectrometric analyses and rules thereof have been studied in detail for a long time, and it is possible to identify the position of an acetyl group based on the fragmentation pattern (B. Lindberg, Methods in Enzymology, Vol. 28, pp. 178–195 (1972)). PMAAs are generated for all monosaccharides constituting an oligosaccharide according to a general methylation analysis. They are usually analyzed using gas chromatography/mass spectrometry (GC/MS) equipment. The position of an acetyl group can be identified based on the fragmentation pattern upon a mass spectrometric analysis. On the other hand, one has to rely on identification by comparison with a standard substance on gas chromatography for identification of the type of the monosaccharide. For this purpose, it is required that all possible PMAAs for all monosaccharides constituting an oligosaccharide have been provided as standard substances. It requires a lot of labor to prepare possible PMAAs for all naturally occurring monosaccharides. In addition, it is practically impossible to conduct chromatography that can be used to separate and identify all possible PMAAs for all naturally occurring monosaccharides.

OBJECTS OF INVENTION

The main object of the present invention is to provide a means that enables determination of the type and the substitution position of a monosaccharide at a reducing end of a saccharide even if the saccharide is not isolated.

SUMMARY OF INVENTION

The present inventors have studied intensively in order to achieve the above-mentioned object. As a result, the present inventors have found that it is possible to determine the type of a monosaccharide at a reducing end of a saccharide according to a method similar to the method as described in WO 96/17824 by converting the saccharide into a hydrazino monosaccharide derivative even if the saccharide is not isolated. Thus, the present invention has been completed.

Accordingly, the present invention provides the following:

(1) a method for producing a hydrazino monosaccharide derivative, the method comprising at least:

(a) reacting a saccharide having a reducing end with a hydrazine of formula (I) to produce a hydrazone:

$$NH_2\text{—}NR^1(R^2) \tag{I}$$

wherein $R^1$ is a group other than hydrogen that has a detectable label and/or an immobilization support as its portion or can bind to a detectable label and/or an immobilization support; the bond between $R^1$ and N is a bond that is cleavable by a reaction that can cleave a glycosidic linkage; and $R^2$ is hydrogen or an alkyl group containing 1–8 carbon atoms;

(b) reducing the hydrazone obtained in step (a) to a hydrazino derivative; and (c) cleaving the hydrazino derivative obtained in step (b) by the reaction that can cleave a glycosidic linkage to obtain a hydrazino monosaccharide derivative;

(2) the method according to (1), which comprises N-acetylating the hydrazino derivative obtained in step (b) before subjecting it to step (c);

(3) the method according to (1) or (2), which comprises methylating a hydroxyl group of the hydrazino derivative obtained in step (b) or an N-acetylation product of the hydrazino derivative before subjecting it to step (c);

(4) the method according to any one of (1) to (3), wherein $R^1$ is an acyl group;

(5) the method according to any one of (1) to (4), wherein $R^1$ is an acyl group that has a ultraviolet or visible-absorbing substance, a fluorescent dye or an immobilization support as its portion;

(6) a method for identifying a monosaccharide at a reducing end of a saccharide having a reducing end and/or for determining a position of binding of a monosaccharide at a reducing end to a neighboring monosaccharide, the method comprising at least:

(a) reacting a saccharide having a reducing end with a hydrazine of formula (I) to produce a hydrazone:

$$NH_2\text{—}NR^1(R^2) \tag{I}$$

wherein $R^1$ is a group other than hydrogen that has a detectable label and/or an immobilization support as its portion or can bind to a detectable label and/or an immobilization support; the bond between $R^1$ and N is a bond that is cleavable by a reaction that can cleave a glycosidic linkage; and $R^2$ is hydrogen or an alkyl group containing 1–8 carbon atoms;

(b) reducing the hydrazone obtained in step (a) to a hydrazino derivative;

(c) cleaving the hydrazino derivative obtained in step (b) by the reaction that can cleave a glycosidic linkage to obtain a hydrazino monosaccharide derivative;

(d) completely acetylating the hydrazino monosaccharide derivative obtained in step (c); and (e) identifying the completely acetylated hydrazino monosaccharide derivative obtained in step (d);

(7) the method according to (6), which comprises N-acetylating the hydrazino derivative obtained in step (b) before subjecting it to step (c);

(8) the method according to (6) or (7), which comprises methylating a hydroxyl group of the hydrazino derivative obtained in step (b) or an N-acetylation product of the hydrazino derivative before subjecting it to step (c), wherein a position of binding of a monosaccharide at a reducing end to a neighboring monosaccharide is determined in step (e);

(9) the method according to any one of (6) to (8), wherein the identification in step (e) is carried out using gas chromatography/mass spectrometry (GC/MS);

(10) a method for labeling a saccharide having a reducing end, the method comprising at least:

(a) reacting a saccharide having a reducing end with a hydrazine of formula (I) to produce a hydrazone:

$$NH_2\text{—}NR^1(R^2) \tag{I}$$

wherein $R^1$ is a group other than hydrogen that has a detectable label and/or an immobilization support as its portion or can bind to a detectable label and/or an immobilization support; the bond between $R^1$ and N is a bond that is cleavable by a chemical reaction that can cleave a glycosidic linkage; and $R^2$ is hydrogen or an alkyl group containing 1–8 carbon atoms;

(b) reducing the hydrazone obtained in step (a) to a hydrazino derivative; and (c) N-acetylating the hydrazino derivative obtained in step (b);

(11) a hydrazine of formula (I) used in the method defined by any one of (1) to (10):

$$NH_2\text{—}NR^1(R^2) \tag{I}$$

wherein $R^1$ is a group other than hydrogen that has a detectable label and/or an immobilization support as its portion or can bind to a detectable label and/or an immobilization support; the bond between $R^1$ and N is a bond that is cleavable by a reaction that can cleave a glycosidic linkage; and $R^2$ is hydrogen or an alkyl group containing 1–8 carbon atoms;

(12) a kit for producing a hydrazino monosaccharide derivative, which contains the hydrazine defined by (11);

(13) a kit for identifying a monosaccharide at a reducing end of a saccharide and/or for determining a position of binding of a monosaccharide at a reducing end to a neighboring monosaccharide, which contains the hydrazine defined by (11);

(14) a kit for labeling a saccharide having a reducing end, which contains the hydrazine defined by (11);

(15) a saccharide of formula (III):

$$R^4\text{—}N(Ac)\text{—}NHR^1 \tag{III}$$

wherein Ac is an acetyl group; $R^1$ is a group other than hydrogen that has a detectable label and/or an immobilization support as its portion or can bind to a detectable label and/or an immobilization support; the bond between $R^1$ and N is a bond that is cleavable by a chemical reaction that can cleave a glycosidic linkage; $R^4$ is a group that may have a glycosidic linkage with a saccharide and from which one hydrogen atom linked to the C-1 position of a 1-deoxy aldose or one hydrogen atom linked to the C-2 carbon of a 2-deoxy ketose is removed, excluding a case where $R^1$ is an acetyl group, and $R^4$ is a group that does not have a glycosidic linkage with a saccharide and from which one hydrogen atom linked to the C-1 position of a 1-deoxy aldose or one hydrogen atom linked to the C-2 carbon of a 2-deoxy ketose is removed; and

(16) the saccharide according (15), wherein $R^1$ is an acyl group.

According to the present invention, it is possible to identify the type of a monosaccharide at a reducing end of a saccharide even if the saccharide is not isolated. Furthermore, a position of binding to a neighboring monosaccharide can be determined by methylating a hydroxyl group of a hydrazino derivative as in the aspect of (7). The identification or determination as described above can be carried out without a need of separation of a reaction product from a reaction mixture by using a hydrazine that has an immobilization support as its portion or contains a group that can bind to an immobilization support.

DETAILED DESCRIPTION OF THE INVENTION

Figure 1:
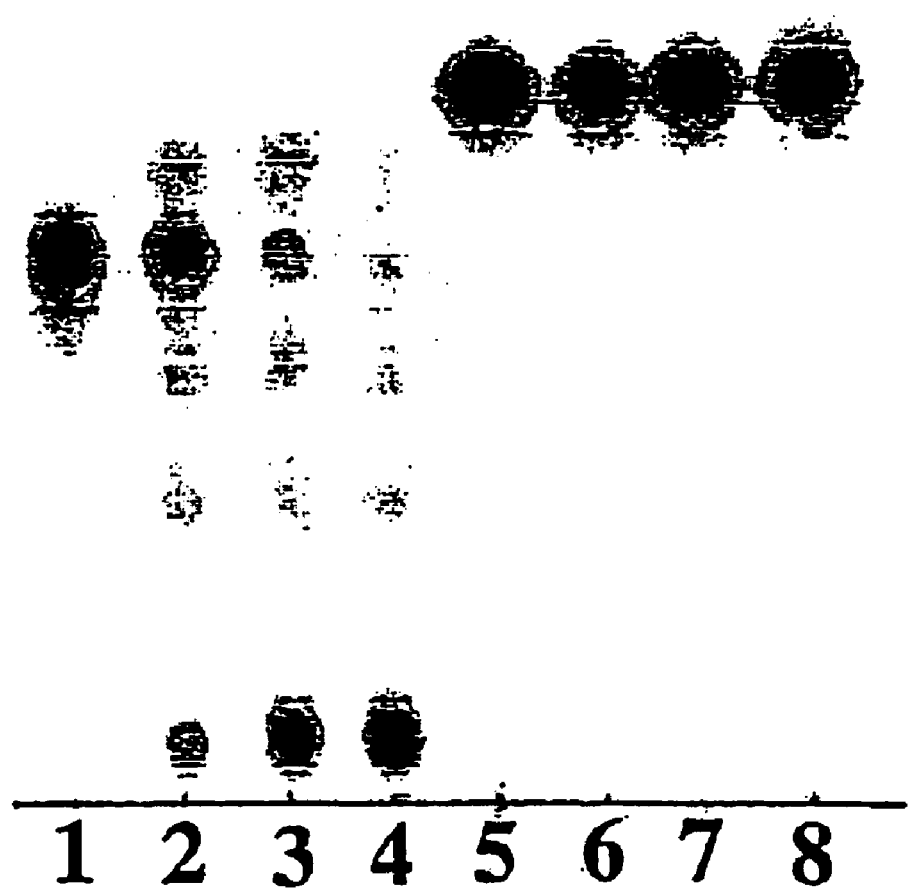
FIG. 1 illustrates thin-layer chromatography on which benzoylhydrazine derivatives of N-acetyl lactosamine which had been allowed to stand under various conditions and N-acetylation products thereof were developed.

A hydrazino monosaccharide derivative produced according to the method of the present invention is used in a method for identifying a monosaccharide at a reducing end as described in WO 96/17824 (JP-A 11-501901, incorporated herein by reference). According to the method as described in WO 96/17824, a hydrazone is produced by reacting an isolated saccharide having a reducing end with a hydrazine, the hydrazone is reduced to a hydrazino derivative, a hydrazino monosaccharide derivative is optionally cleaved from an oligosaccharide, the hydrazino monosaccharide derivative is acetylated to obtain an N,N'-diacetylhydrazino monosaccharide derivative, and the diacetylhydrazino monosaccharide derivative is identified by means of GC/MS or the like.

There is no specific limitation concerning the saccharide having a reducing end used in step (a) of the method for producing a hydrazino monosaccharide derivative of the present invention. It may be any saccharide of which the monosaccharide at the reducing end is to be identified and/or the position of binding of the monosaccharide at the reducing end to a neighboring monosaccharide is to be determined. Such saccharides include monosaccharides, oligosaccharides and polysaccharides as well as mixtures thereof. A sample containing a saccharide used in the method of the present invention may further contain other components derived from a natural source (proteins, nucleic acids, etc.). A method for obtaining a sample containing a saccharide used in the method of the present invention from a natural source is described, for example, in "Seikagaku jikken koza 4—Toshitsu no kagaku (Jo)", edited by the Japan Biochemical Society, published on Apr. 12, 1976, Tokyo Kagaku Dozin.

As used herein, the phrase "a monosaccharide at a reducing end" refers to a monosaccharide having a reducing property located at a terminus (a reducing end) of a saccharide in which the C-1 position of an aldose or the C-2 position of a ketose is not subjected to substitution. An "aldose" refers to either a free monosaccharide or a monosaccharide at a reducing end of an oligosaccharide that may have an aldehyde group at the C-1 position. A "ketose" refers to either a free monosaccharide or a monosaccharide at a reducing end of an oligosaccharide that may have a ketone group at any one of internal carbon atoms along the backbone of the monosaccharide.

A hydrazine that is structurally different from the hydrazine used in the method as described in WO 96/17824 is used in the method for producing a hydrazino monosaccharide derivative of the present invention. Thereby, the need of isolating a saccharide to be analyzed beforehand is eliminated. A "hydrazine" generally means a compound generated by substituting an organic group for a hydrogen atom of hydrazine (in a narrow sense, $N_2H_4$). A "hydrazine" used in the method for producing a hydrazino monosaccharide derivative of the present invention is any known or novel compound represented by formula (I):

$$NH_2—NR^1(R^2) \qquad (I)$$

wherein $R^1$ is a group other than hydrogen that has a detectable label and/or an immobilization support as its portion or can bind to a detectable label and/or an immobilization support; the bond between $R^1$ and N is a bond that is cleavable by a reaction that can cleave a glycosidic linkage; and $R^2$ is hydrogen or an alkyl group containing 1–8 carbon atoms. Only one of four hydrogen atoms of hydrazine (in a narrow sense, $N_2H_4$) in the hydrazine used in the method as described in WO 96/17824 may be replaced by an alkyl group containing 1–8 carbon atoms.

A "detectable label" is any label known in the art that facilitates the purification of a hydrazino derivative. Examples thereof include ultraviolet or visible-absorbing labels (e.g., benzene and derivatives thereof), fluorescent labels (e.g., fluoresceine, pyrene, anthracene and derivatives thereof), and radioactive labels (e.g., radioactive hydrogen, radioactive carbon and radioactive iodine) as well as a biotin label and a digoxigenin label. If it is desired that a detectable label would be attached after a hydrazino derivative is produced, a hydrazine containing a group that can bind to a detectable label and a detectable group may exist independently. Alternatively, a group that has a detectable label as its portion may be used. An acyl group that has a fluorescent dye as its portion exemplifies a group that has a detectable label as its portion. For example, a hydrazino derivative can be readily purified by using a method known in the art such as normal phase high performance liquid chromatography using fluorescence emitted from pyrene attached using 1-pyrenebutanoic acid, hydrazide (commercially available from Molecular Probes) as an index. In addition, many compounds such as biotin-hydrazide (Dojindo), benzoylhydrazine (Tokyo Kasei Kogyo) Cascade Blue hydrazide (Molecular Probes) are available as acylhydrazides having detectable groups.

Those skilled in the art can readily obtain a hydrazine compound to be used for labeling a detectable label by synthesizing it. For example, an acylhydrazide can be readily obtained by attaching a compound having carboxylate as a functional group to hydrazine (in a narrow sense, $N_2H_4$) using a technique used for peptide synthesis (Izumiya et al., "Peptide gousei no kiso to jikken" (1985) Maruzen). A compound having an amino group as a functional group can be condensed with hydrazine (in a narrow sense, $N_2H_4$) according to the above-mentioned method, for example, after the functional group is converted to carboxylate using succinic anhydride. In addition, hydrazine (in a narrow sense, $N_2H_4$) can be introduced to a compound having a hydroxyl group as a functional group by halogenation followed by a reaction with carbohydrazide ($H_2N—NH—CO—NH—NH_2$).

The above-mentioned techniques for synthesizing a hydrazine compound can be applied not only in case of a detectable labeling compound but also in case of an immobilization support.

Any or all of reaction steps of the method of the present invention may be conducted in a liquid phase or in a solid phase. An "immobilization support" may be used for conducting various reactions on hydrazino derivatives in a solid phase. For example, a position of binding of a monosaccharide at a reducing end to a neighboring monosaccharide can be determined in step (e) of the method for identifying a monosaccharide at a reducing end and/or for determining a position of binding of a monosaccharide at a reducing end to a neighboring monosaccharide of the present invention as described below in detail. The determination can be accomplished by methylating a hydroxyl group of the hydrazino derivative obtained in step (b) before subjecting the hydrazino derivative to step (c). In general, the methylation reaction involves several steps of reaction/washing. A procedure for separating a reaction product from a reaction mixture in each step can be omitted by attaching a hydrazino derivative to an immobilization support.

If a hydrazino derivative attached to an immobilization support can be purified, the saccharide to be used need not be isolated. Generally, a hydrazine that has an immobilization support as its portion or contains a group capable of binding to an immobilization support is used for an isolated saccharide. If a saccharide is not isolated, one can label a mixture containing the saccharide with a hydrazine compound containing a detectable label, purify a hydrazino-derivatized saccharide using the label as an index, and attach the purified hydrazine-derivatized saccharide to an immobilization support. For example, if a saccharide is reacted with an excess amount of 4-aminobenzhydrazide, the saccharide is preferentially condensed with a hydrazide group to form a hydrazone. After reduction, a saccharide hydrazino derivative can be purified using ultraviolet absorbance of a benzene ring as an index. The purified saccharide hydrazino derivative can be attached through an amino group of the derivative, for example, to an immobilization support having N-hydroxy succinimide ester as a functional group. Immobilization supports include glass beads, polymer matrixes, sintered glass disks, fiber glass membranes and polymer membranes. It is usually desirable that the immobilization support has a functional group for immobilizing a hydrazine or a saccharide hydrazino derivative. Examples of such functional groups include an amino group, a carboxyl group, a hydroxyl group and an alkyl halide group. Examples of immobilization supports having such functional groups include NovaSyn TG bromo Resin commercially available from Nova Biochem and Bio-Rex 70 Resin commercially available from Bio-Rad. A hydrazine having such an immobilization support as its portion is produced, for example, according to the procedure as described in Example 2. The reducing power of the thus obtained hydrazine can be measured according to a method known in the art such as the Park-Johnson method (Park, J. T. and Johnson, M. J., J. Biol. Chem., 181, 149–151 (1949)).

The reaction of a saccharide having a reducing end with a hydrazine in step (a) is conducted under appropriate conditions known to those skilled in the art, for example, in an appropriate solvent (e.g., DMSO or acetonitrile) at 40–90° C. for 0.1–20 hours. For example, the reaction is conducted by heating in dimethyl sulfoxide (DMSO) containing 10% acetic acid at 90° C. for 1 hour.

The reduction of a hydrazone to a hydrazino derivative in step (b) can be conducted using any appropriate reducing agent known to those skilled in the art. Examples of appropriate reducing agents include boron hydride reagents, boron-centered hydrides, borane/diborane, aluminum hydride reagents, and other aluminum-centered hydrides having alkoxy groups that cause substitution with covalently bound carbon or hydrogen. Catalytic hydrogenation can be conducted using hydrogen gas and one of various metals or a prepared alloy such as Raney nickel (a nickel-aluminum alloy). In addition, dissolution of a reduced metal, use of an alkaline metal (lithium, sodium or potassium) and, for example, zinc, magnesium, tin, iron or mercury in a solvent (e.g., an alcohol, acetic acid, liquid ammonia or an ether such as 1,2-dimethoxyethane) are generally effective.

A reduction reaction is conducted in an appropriate solvent (e.g., DMSO or water) at 20 to 90° C. for 1 to 20 hours. For example, it is conducted by heating in a solution containing 2.5 M borane-dimethylamine complex and 30% acetic acid in DMSO at 80° C. for 1 hour or by allowing to stand in a 1 M sodium boron hydride aqueous solution at room temperature for 16 hours. Those skilled in the art understand that the time required for such a reaction may be shortened or prolonged depending on the elevation or lowering of temperature. The product and the yield in a reduction step can be monitored using an analytical technique such as proton NMR or mass spectrometry.

It is well known to those skilled in the art that steps (a) and (b) may be carried out not only as separate steps but also as steps proceeding in parallel.

Furthermore, a hydrazino derivative may be N-acetylated after a reduction reaction, if necessary. It is expected that the N-acetylation of a hydrazine derivative is effective in loss of charge and chemical stabilization.

A hydrazino derivative is cleaved by a reaction that can cleave a glycosidic linkage to obtain a hydrazino monosaccharide derivative in step (c). The bond between $R^1$ and N contained in the hydrazine used in step (a) is also cleaved at the same time. Any reaction that can cleave a glycosidic linkage known to those skilled in the art can be used (see, for example, Biermann, C. J., Advances in Carbohydrate Chemistry and Biochemistry, Vol. 46, 251–271). $R^1$ is appropriately selected by those skilled in the art such that the bond between $R^1$ and N can be cleaved under the selected reaction conditions. In one embodiment, $R^1$ is an acyl group. In another embodiment, $R^1$ is an acyl group that has a detectable label (a fluorescent dye or an immobilization support) as its portion. The step of cleavage can be accomplished by using acidic conditions in one of various solvents such as water, an alcohol or carboxylic acid. Appropriate cleaving agents include a solution of hydrochloric acid or trifluoroacetic acid in water, hydrochloric acid in absolute methanol, and sulfuric acid in an acetic anhydride solution. The cleavage is generally conducted at 50 to 110° C. for 1 to 10 hours. For example, the cleavage is conducted by heating in 5% hydrochloric acid-methanol at 90° C. for 4 hours or by heating in 4 M hydrochloric acid at 100° C. for 4 hours.

A hydrazino monosaccharide derivative obtained by a method comprising steps (a) to (c) is represented by formula (II):

$$R^3-NH-NH-R^2 \qquad (II).$$

Therein, $R^3$ is a 1-deoxy aldose moiety or a deoxy ketose moiety covalently bound to N in the formula. If $R^3$ is a 1-deoxy aldose moiety, the covalent binding to N is generated through the C-1 position. If $R^3$ is a deoxy ketose moiety, the covalent binding to N is generated through the deoxy carbon in the sugar backbone (which carbon is originally present in the ketone group). In all cases, $R^2$ is hydrogen or an alkyl group containing 1–8 carbon atoms.

Among hydrazino monosaccharide derivatives of formula (II), a hydrazino monosaccharide derivative having a structure in which all or some of hydroxyl groups of the 1-deoxy aldose moiety or the deoxy ketose moiety represented by $R^3$ are methylated is designated as an "O-methylated hydrazino monosaccharide derivative" in particular.

The aldose or the ketose constituting the group represented by $R^3$ may be any monosaccharide in a free form or at a reducing end of an oligosaccharide. Examples of aldoses include the following: aldohexoses each containing 6 carbon atoms (e.g., D-glucose, L-glucose, D-allose, D-altrose, D-galactose, D-gulose, D-idose, D-mannose and D-talose); aldopentoses each containing 5 carbon atoms (e.g., D-arabinose, D-lyxose, D-ribose and D-xylose); aldotetroses each containing 4 carbon atoms (e.g., D-erythrose and D-threose); and aldotrioses each containing 3 carbon atoms (e.g., D-glyceraldehyde). Ketoses include ketohexoses each containing 6 carbon atoms (e.g., D-fructose, D-psicose, D-sorbose and D-tagatose).

Using the hydrazino monosaccharide derivative obtained as described above, identification of a monosaccharide at a reducing end of a saccharide having a reducing end and/or determination of a position of binding of a monosaccharide at a reducing end to a neighboring monosaccharide is carried out as follows.

A hydrazino monosaccharide derivative is completely acetylated in step (d). The term "acetylation" refers to covalent binding of one or more acetyl groups to a molecule. A "completely acetylated" molecule is a molecule in which all of the free hydroxyl groups and the nitrogen atoms are acetylated.

Any appropriate O-acetylation reaction known in the art can be used for completely acetylating the derivative. Such reactions include, but are not limited to, reactions with an acetic anhydride/pyridine mixture, acetic anhydride, zinc chloride, sodium acetate, sulfuric acid, or acetyl chloride in a pyridine solution (see, for example, Horton D. IA, "The Amino Sugars", pp. 3–211, R. W. Jeanloz (ed.), Academic Press, 1969; incorporated herein by reference).

N-acetylation takes place more readily than O-acetylation. Therefore, complete acetylation of deoxy-hydrazino alditol and deoxy-(N'-alkyl hydrazino) alditol takes place under the conditions as described above for "O-acetylation" to generate acetyl groups on all of the nitrogen atoms and the free hydroxyl groups in the molecule.

For example, O-acetylation is carried out by adding a 2:1 mixture of pyridine and acetic anhydride to a sample and incubating the resulting mixture at 37° C. for 16 hours.

If N-acetylation is to be conducted selectively without effecting O-acetylation, the N-acetylation is conducted, for example, by mixing with acetyl anhydride in a weak alkaline buffer. Saturated sodium bicarbonate is preferably used as a weak alkaline buffer. Unless otherwise stated, as used herein, "N-acetylation" means acetylation selective for nitrogen atoms.

The hydrazino derivative obtained in step (b) may be methylated at the hydroxyl group before subjecting it to step (c) in the method of the present invention. As a result of the methylation, it is possible to determine the position of binding of a monosaccharide at a reducing end to a neighboring monosaccharide (or the "substitution position") in step (e).

The "methylation analysis" by which the position of binding between monosaccharides constituting a saccharide is determined is useful for determining a position of binding of a monosaccharide at a reducing end to a neighboring monosaccharide. According to this method, a free hydroxyl group of a reducing sugar is first methylated completely, the resulting methylated saccharide is cleaved to generate a partially methylated monosaccharide in which only the hydroxyl group at the position of binding to a neighboring monosaccharide is free, the partially methylated monosaccharide is acetylated, and the position of acetylation is identified. Methylation is conducted by any method known in the art. For example, methylation can be conducted using the method of Hakomori (S. Hakomori, J. Biochem. (Tokyo), Vol. 55, 205–208 (1964)), the DMSO-NaOH method (I. Ciucanu and F. Kerek, Carbohydrate Research, Vol. 131, 209–217 (1984)), or the method of Anumula et al. (an improved DMSO-NaOH method) (Anumula, K. R. and Taylor, P. B., Anal. Biochem., Vol. 203, 101–108 (1992)) (incorporated herein by reference).

According to the method for determining a position of binding of a saccharide at a reducing end to a neighboring monosaccharide of the present invention, if $R_1$ is an acyl group and the DMSO-NaOH method or the method of Anumula et al. is used as a means of methylation, the completely acetylated hydrazino monosaccharide derivative cannot be identified later in step (e) unless the nitrogen atom (N) directly bound to the sugar of the hydrazino derivative is acetylated prior to methylation. Acetylation may be either N-acetylation or complete acetylation in this case. This is because an O-acetyl group introduced by complete acetylation is immediately detached under strongly basic conditions used for methylation and a methyl group is introduced in place of the O-acetyl group. N-acetyl groups remain to be attached under these conditions.

Those skilled in the art can readily carry out N-acetylation of a hydrazino derivative. For example, N-acetylation of a hydrazino oligosaccharide derivative can be conducted according to the method as described in WO 96/17824 (JP-A 11-501901). Alternatively, a hydrazino oligosaccharide derivative may be completely acetylated by a method well known to those skilled in the art, for example, by allowing it to stand in a 2:1 mixture of pyridine and acetic acid at 37° C. overnight.

The present inventors have found another unexpected effect of acetylation of a nitrogen atom (N) directly bound to a carbon atom derived from a saccharide in a hydrazino derivative. Specifically, the chemical stability of a hydrazino derivative was increased by acetylating a nitrogen atom (N) directly bound to a carbon atom derived from a saccharide in the hydrazino derivative. A phenomenon that an N-acetylated hydrazino derivative is very stable whereas a saccharide hydrazino derivative is unstable in an acidic solution was observed. Furthermore, it is additionally advantageous that an N-acetylated hydrazino derivative results in a sharper peak or band as compared with a hydrazino derivative that is not N-acetylated. This is because an N-acetylated hydrazino derivative does not have a charge due to protonation of a nitrogen atom and thus does not interact with a carrier upon chromatography for purification or analysis.

A monosaccharide at a reducing end of a saccharide having the reducing end can be identified by identifying, in step (e), the completely acetylated hydrazino monosaccharide derivative obtained as described above. Furthermore, the position of binding of a monosaccharide at a reducing end to a neighboring monosaccharide can be determined by methylating a hydrazino derivative at a hydroxyl group as described above.

The derivative of the present invention may be purified prior to analysis. Alternatively, it may not necessarily be purified if a system in which chromatography is connected to analytical equipment such as gas chromatography/mass spectrometry (GC/MS) or liquid chromatography/mass spectrometry (LC/MS) (generically called an on-line mass spectrometric analysis) is used. The completely acetylated hydrazino monosaccharide derivative may be purified prior to or following acetylation. The derivative is purified using preferably chromatography, more preferably high performance liquid chromatography.

A completely acetylated hydrazino monosaccharide derivative can be used for determining the structure of the monosaccharide. A method for determining the structure preferably comprises separation by chromatography and a mass spectrometric analysis. More preferably, separation is accomplished by gas chromatography (GC/MS).

A derivative is detected using any appropriate technique known to those skilled in the art. Preferably, the detection is typically carried out using ultraviolet absorbance at 200 nm or mass spectrometry (MS). Detection of a derivative using an on-line mass spectrometric analysis such as GC/MS or LC/MS (i.e., directly introducing a compound separated by chromatography into a mass spectrometer for analysis) is particularly preferable.

In a mass spectrometric analysis, a sample in a gas state is ionized in vacuo by a method such as electron impact (EI) or chemical ionization (CI), and the resulting ion is detected. In case of an on-line mass spectrometric analysis, a molecule separated by chromatography is ionized by electron impact (EI) or chemical ionization (CI). The amount of a sample required for analysis is usually less than 1 pmol. For review on basic equipment, see Cooks, R. G., Glish, G. L., McLucky, S. A. and Kaiser, R. E., Chemical and Engineering News, Mar. 25, 1991, pp. 26–41 (incorporated herein by reference).

Unlike a general methylation analysis as described in the Background Art section, it is intended to carry out a methylation analysis only for a monosaccharide at a reducing end according to the method for determining a binding position of a saccharide of the present invention. The type of a monosaccharide at a reducing end can be identified by converting an oligosaccharide to a hydrazino derivative, cleaving the resulting hydrazino oligosaccharide derivative by a reaction that can cleave a glycosidic linkage, obtaining a hydrazino monosaccharide derivative, completely acetylating the hydrazino monosaccharide derivative and subjecting the product to GC/MS (Bendiak, B. and Fang, T. T., Carbohydr. Res. 327, 463–481 (2000)). The position of binding of a monosaccharide at a reducing end to a neighboring monosaccharide can be determined by a procedure almost the same as that of a general methylation analysis. Specifically, analysis is carried out by converting an oligosaccharide to a hydrazino derivative, completely methylating the resulting hydrazino oligosaccharide derivative, cleaving the completely methylated hydrazino oligosaccharide derivative by a reaction that can cleave a glycosidic linkage, obtaining a partially methylated hydrazino monosaccharide derivative, completely acetylating it and subjecting the partially methylated/acetylated hydrazino monosaccharide derivative (partially methylated 1-deoxy-1-hydrazino alditol acetates, or partially methylated 2-deoxy-2-hydrazino alditol acetates, PMHAA) to GC/MS. A saccharide other than the saccharide at the reducing end which may be detected by the above-mentioned procedure as a partially methylated/acetylated saccharide can be distinguished from the partially methylated/acetylated hydrazino monosaccharide derivative based on the retention time on GC or the mass spectrum. Distinction based on a mass spectrum is particularly effective. For example, a molecular ion mass of PMHAA can be detected by determining a positive ion mass spectrum by chemical ionization using isobutane. If the type of a monosaccharide at a reducing end has been identified by a reducing end analysis, the number of possible molecular ion masses for the expected PMHAAs is limited to 6 at the most. Then, the peak for the PMHAA can be readily identified by scanning the chromatogram for the mass.

The position of an acetyl group in a PMHAA can be identified based on a fragmentation pattern obtained by determining an MS/MS spectrum of a detected molecular ion.

It is basically possible to apply fragmentation patterns for PMAAs upon mass spectrometric analyses and rules thereof, which have been conventionally examined in detail, to fragmentation patterns for PMHAAs upon MS/MS. However, there has been no report on obtainment of a PMHAA, and details of the fragmentation patterns unique to the PMHAAs upon mass spectrometric analyses and rules thereof have not been examined yet at all.

A PMHAA can be produced using an N,N'-diacetylated hydrazino oligosaccharide (e.g., 1-deoxy-1-(N,N'-diacetyl hydrazino)-lactitol) as a raw material. The method disclosed in WO 96/17824 (JP-A 11-501901) can be used as a method for producing an N,N'-diacetylated hydrazino oligosaccharide. An N,N'-diacetylated hydrazino oligosaccharide is completely methylated, and a partially methylated hydrazino monosaccharide is then obtained, for example, by a glycosidic linkage-cleaving reaction such as methanolysis. A PMHAA can be obtained by completely acetylating the resulting partially methylated hydrazino monosaccharide. The thus obtained PMHAA may be used as it is, or it may be used after further purification by chromatography such as reverse phase high performance liquid chromatography.

One of properties of PMHAAs is that they are less volatile. Due to this property, mild distillation-removal of a solvent by nitrogen blowing which is required for a PMAA is not necessary. Loss of a sample is not observed at all even if drying under reduced pressure using a centrifugation concentrator is carried out.

The present invention also relates to a hydrazine, a kit used in the method of the present invention as described above. The kit contains said hydrazine as an essential component, and is for producing a hydrazino monosaccharide derivative or for identifying a monosaccharide at a reducing end of a saccharide and/or for determining a position of binding of a monosaccharide at a reducing end to a neighboring monosaccharide. The kit may further contain an additional reagent to be used for a reaction in each step, a reaction vessel, instructions and the like.

EXAMPLES

The following examples further illustrate the present invention in detail but are not to be construed to limit the scope thereof.

Example 1

Preparation and Analysis of Hydrazino Glucose Derivative (a) Preparation of Hydrazone 20 $\mu$l of a 4 $\mu$M 1-pyrenebutanoic acid, hydrazide (Molecular Probes) solution in dimethyl sulfoxide (DMSO) was added to 360 $\mu$g of glucose which had been dried adequately, and glucose was fully dissolved by sonication. 2 $\mu$l of acetic acid was added thereto and the mixture was stirred adequately. The reaction mixture was then heated at 90° C. for 1 hour.

(b) Reduction of Hydrazone

The reaction mixture obtained in (a) was dried using a centrifugation concentrator. 20 µl of a solution containing 2.5 M borane-dimethylamine complex and 30% acetic acid in DMSO was added to the residue, and the residue was fully dissolved by sonication. The mixture was then heated at 80° C. for 1 hour. The reaction mixture was dried using a centrifugation concentrator. The residue was re-dissolved in 50% acetonitrile and purified using normal phase high performance liquid chromatography. The existence of pyrene-labeled glucose was confirmed by determining the molecular weight of the purified product using a triple-quadrupole ion-spray mass-spectrometer API-300 (Perkin-Elmer Sciex) to detect a positive molecular ion (467.0).

(c) Methanolysis of Pyrene-Labeled Glucose

The purified pyrene-labeled glucose obtained in (b) (10 nmol) was placed in a glass test tube and dried. 100 µl of 5% hydrochloric acid-methanol (Nacalai Tesque) was added to the test tube. The tube was sealed and heated at 90° C. for 4 hours. The tube was opened, and the sample was dried using a centrifugation concentrator to obtain a cleavage product.

(d) GC/MS Analysis 10 nmol of 1-deoxy-1-(N,N'-diacetyl hydrazino)-$^{13}C_6$-D-glusitol as an internal standard was added to the residue obtained after methanolysis of the pyrene-labeled glucose in (c), and the mixture was dried again. 1-deoxy-1-(N,N'-diacetyl hydrazino)-$^{13}C_6$-D-glusitol was prepared according to a known method (JP-A 11-501901; incorporated herein by reference) using $^{13}C_6$-D-glucose (Aldrich) as a starting material. 100 µl of a 2:1 mixture of pyridine and acetic anhydride was added to the resulting residue. After adequately stirring, the mixture was incubated at 37° C. for 16 hours. The sample was dried using a centrifugation concentrator. The residue was dissolved by adding 200 µl of chloroform thereto. 1 µl of the solution was analyzed by subjecting it to GC/MS by splitless injection. GC/MS analysis was carried out as follows:

System: GCQ (Finnigan MAT)
Column: DB-5 (5% diphenyl-95% dimethyl polysiloxane, 0.25 mm i.d.×30 m, 0.25 micrometer film thickness) (J & W Scientific)
Carrier: Herium (40 cm/sec)
Ionization: EI
Injector temperature: 300° C.
Column initial temperature: 90° C.
Time program: 90° C. for 2 min, 90° C.—(24° C./min)—210° C., and 210° C.—(4° C./min)—300° C.
Injection: 1 microliter (splitless injection)

Main peaks were observed at 16.04 minutes and 21.21 minutes in a total ion mass chromatogram. A peak was observed at 16.04 minutes in a single mass chromatogram for a specific ion ($[M-42]^+$) at m/z=448 for completely acetylated 1-deoxy-1-(N,N'-diacetyl hydrazino)-$^{12}C_6$-D-glusitol. This peak was consistent with a peak in a single mass chromatogram for a specific ion ($[M-42]^+$) at m/z=454 for completely acetylated 1-deoxy-1-(N,N'-diacetyl hydrazino)-$^{13}C_6$-D-glusitol from the internal standard. The peak at 21.21 minutes had a main ion of m/z=302 which was consistent with the molecular ion of 1-pyrenebutanoic acid methyl ester.

Example 2

Hydrazine-Immobilized Support (a) Preparation of Carbohydrazide-Immobilized NovaSyn TG Resin 360 mg of NovaSyn TG bromo Resin (Nova Biochem) was suspended in a 0.5 M carbohydrazide (Aldrich) solution in DMSO. The mixture was shaken at room temperature for 16 hours. The resin was washed in sufficient amounts of DMSO, water and ethanol, treated with a 15 mg/ml cesium acetate/dimethylformamide (DMF) solution, and then washed in sufficient amounts of DMF, water and ethanol to obtain carbohydrazide-immobilized NovaSyn TG Resin. The reducing power of carbohydrazide being introduced was measured according to the Park-Johnson method (Park, J. T. and Johnson, M. J., J. Biol. Chem., 181, 149–151 (1949)). As a result, a reducing power corresponding to 1.1 nmol of 4-methoxyphenylhydrazine hydrochloride was observed for 1 mg of the resin.

(b) Preparation of Hydrazine-Immobilized Bio-Rex 70 Resin 200 mg of Bio-Rex 70 Resin (Bio-Rad) of which the ion type had been converted into a proton form was suspended in 5 ml of N,N-dimethylformamide (DMF). 0.5 g of 1-ethyl-3-(3-dimethylaminopropyl)carbodiimide hydrochloride (EDC) (Nacalai Tesque) was added thereto. The mixture was shaken at room temperature for 16 hours. The resin was washed in 20 ml of DMF. 5 ml of a 10% hydrazine (Nacalai Tesque) solution in DMF was then added thereto. The mixture was shaken for additional 5 hours. The resin was washed in sufficient amounts of DMF, water, 1 M hydrochloric acid, water and methanol to obtain hydrazine-immobilized Bio-Rex 70 Resin. The reducing power of hydrazine being introduced was measured according to the Park-Johnson method (Park, J. T. and Johnson, M. J., J. Biol. Chem., 181, 149–151 (1949)). As a result, a reducing power corresponding to 27.6 nmol of 4-methoxyphenylhydrazine hydrochloride was observed for 1 mg of the resin.

(c) Attachment of Saccharide to Resin

100 µl of a solution containing 100 mM glucose and 10% acetic acid in DMSO was added to 10 mg of the hydrazine-immobilized Bio-Rex 70 Resin obtained in (b). The mixture was heated at 90° C. for 1 hour. The resin was washed in 50 ml of DMSO. 1 ml of a 1 M sodium boron hydride aqueous solution was then added the resin. The mixture was allowed to stand at room temperature for 16 hours. The resin was washed in sufficient amounts of water, 0.1 M hydrochloric acid, water, and ethanol, and dried.

(d) Acid Hydrolysis of Saccharide-Attached Resin

The dried saccharide-attached resin obtained in (c) was transferred to a glass test tube. 100 µl of 4 M hydrochloric acid was added thereto. The tube was sealed and heated at 100° C. for 4 hours. After the tube was opened, a supernatant was recovered and dried under reduced pressure to obtain a hydrolysis product.

(e) GC/MS Analysis

100 µl of a 2:1 mixture of pyridine and acetic anhydride was added to the residue obtained after hydrolysis in (d). After adequately stirring, the mixture was allowed to stand at room temperature for 16 hours. The sample was dried using a centrifugation concentrator. The residue was dissolved by adding 200 µl of acetonitrile thereto. 1 µl of the solution was analyzed by subjecting it to GC/MS by splitless injection. GC/MS analysis was carried out as follows:

System: GCQ (Finnigan MAT)
Column: DB-5 (5% diphenyl-95% dimethyl polysiloxane, 0.25 mm i.d.×30 m, 0.25 micrometer film thickness) (J & W Scientific)
Carrier: Herium (40 cm/sec)
Ionization: EI
Injector temperature: 300° C.
Column initial temperature: 90° C.
Time program: 90° C. for 2 min, 90° C.—(24° C./min)—210° C., and 210° C.—(4° C./min)—300° C.
Injection: 1 microliter (splitless injection)

A peak was observed at 14.5 minutes in a single mass chromatogram for a specific ion ($[M-42]^+$) at m/z=448 for completely acetylated 1-deoxy-1-(N,N'-diacetyl hydrazino)-D-glusitol. The mass chromatogram for this peak was consistent with that for completely acetylated 1-deoxy-1-(N,N'-diacetyl hydrazino)-D-glusitol as a standard.

Example 3
Methylation Analysis (a) Preparation of Pyrene-Labeled Lactose

10 µl of a solution containing 400 nmol of 1-pyrenebutanoic acid, hydrazide (Molecular Probes) in DMSO was added to 50 nmol of lactose which had been dried adequately, and lactose was fully dissolved by sonication. 1 µl of acetic acid was added thereto and the mixture was stirred adequately. The reaction mixture was then heated at 90° C. for 1 hour. After the reaction mixture was dried using a centrifugation concentrator, 10 µl of a solution containing 2.5 M borane-dimethylamine complex and 30% acetic acid in DMSO was added to the residue, and the residue was fully dissolved by sonication. The mixture was then heated at 80° C. for 1 hour. The reaction mixture was dried using a centrifugation concentrator. The residue was re-dissolved in 50% acetonitrile and purified using normal phase high performance liquid chromatography. The molecular weight of the purified pyrene-labeled lactose was determined using a triple-quadrupole ion-spray mass-spectrometer API-300. As a result, a positive molecular ion (629.3) was observed.

(b) Methanolysis of Pyrene-Labeled Lactose

The purified pyrene-labeled lactose obtained in (a) (20 nmol) was placed in a glass test tube and dried. 100 µl of 5% hydrochloric acid-methanol (Nacalai Tesque) was added to the test tube. The tube was sealed and heated at 90° C. for 4 hours. The tube was opened, and the sample was dried using a centrifugation concentrator to obtain a cleavage product.

(c) GC/MS Analysis

100 µl of a 2:1 mixture of pyridine and acetic anhydride was added to the residue obtained after methanolysis of the pyrene-labeled lactose. After adequately stirring, the mixture was incubated at 37° C. for 16 hours. The sample was dried using a centrifugation concentrator. The residue was dissolved by adding 200 µl of acetonitrile thereto. 1 µl of the solution was analyzed by subjecting it to GC/MS by splitless injection. GC/MS analysis was carried out as follows:
System: GCQ (Finnigan MAT)
Column: DB-5 (5% diphenyl-95% dimethyl polysiloxane, 0.25 mm i.d.×30 m, 0.25 micrometer film thickness) (J & W Scientific)
Carrier: Herium (40 cm/sec)
Ionization: CI (Isobutane)
Injector temperature: 300° C.
Column initial temperature: 90° C.
Time program: 90° C. for 2 min, 90° C.—(24° C./min)—210° C., and 210° C.—(4° C./min)—300° C.
Injection: 1 microliter (splitless injection)

Main peaks were observed at 8.1 minutes, 14.6 minutes and 20.1 minutes in a total ion mass chromatogram. A peak was observed at 14.6 minutes in a single mass chromatogram for a positive molecular ion ([M+H]$^+$) at m/z=491 for completely acetylated 1-deoxy-1-(N,N'-diacetyl hydrazino)-D-glusitol. Both the retention time and the mass spectrum were consistent with those for the completely acetylated 1-deoxy-1-(N,N'-diacetyl hydrazino)-D-glusitol as a standard.

(d) Methylation of Pyrene-Labeled Lactose 100 nmol of the purified pyrene-labeled lactose obtained in (a) was placed in a screw-capped glass test tube and dried under reduced pressure. 200 µl of a 2:1 mixture of pyridine and acetic anhydride was added to the residue. After adequately stirring, the mixture was allowed to stand at room temperature for 16 hours. The sample was dried using a centrifugation concentrator. 100 µl of methanol was added to the residue, and the mixture was dried again. The thus obtained sample was subjected to complete methylation treatment of the pyrene-labeled lactose using the method of Anumula et al. (Anumula, K. R. and Taylor, P. B., Anal. Biochem., 203, 101–108 (1992)). A product obtained after extraction with chloroform was dried under reduced pressure.

(e) Methanolysis of Methylated Pyrene-Labeled Lactose

The methylated pyrene-labeled lactose obtained in (d) (corresponding to 50 nmol) was placed in a glass test tube and dried. 100 µl of 5% hydrochloric acid-methanol (Nacalai Tesque) was added to the test tube. The tube was sealed and heated at 90° C. for 4 hours. The tube was opened, and the sample was dried using a centrifugation concentrator to obtain a cleavage product.

(f) GC/MS Analysis

100 µl of a 2:1 mixture of pyridine and acetic anhydride was added to the residue obtained in (e) after methanolysis of the methylated pyrene-labeled lactose. After adequately stirring, the mixture was allowed to stand at room temperature for 16 hours. The sample was dried using a centrifugation concentrator. The residue was dissolved by adding 200 µl of acetonitrile thereto. 1 µl of the solution was analyzed by subjecting it to GC/MS by splitless injection. GC/MS analysis was carried out as follows:
System: GCQ (Finnigan MAT)
Column: DB-5 (5% diphenyl-95% dimethyl polysiloxane, 0.25 mm i.d.×30 m, 0.25 micrometer film thickness) (J & W Scientific)
Carrier: Herium (40 cm/sec)
Ionization: CI(Isobutane)
Injector temperature: 300° C.
Column initial temperature: 90° C.
Time program: 90° C. for 2 min, 90° C.—(24° C./min)—210° C., and 210° C.—(4° C./min)—300° C.
Injection: 1 microliter (splitless injection)

An m/z value of 393 corresponding to a positive molecular ion peak ([M+H]$^+$) for 4-O-acetyl-1-deoxy-2,3,5,6-O-tetramethyl-1-(N,N'-diacetyl-N'-methylhydrazino)-D-glusitol was observed when the main peak observed at 11.3 minutes was subjected to mass spectrometry.

Example 4
Preparation of Partially Methylated/Acetylated Hydrazino Monosaccharide Derivative (Partially Methylated 1-deoxy-1-hydrazino Alditol Acetates, PMHAA)

10 µmol each of lactose(Galβ1-4Glc) (Nacalai Tesque), mannobiose (Manα1-2Man) (Dextra Laboratories), mannotriose (Manα1-6[Manα1-3]Man) (Dextra Laboratories) and N-acetyl lactosamine (Galβ1-4GlcNAc) (Seikagaku Corporation) was converted to an N,N'-diacetylated hydrazino derivative according to the method as described in WO 96/17824 (JP-A 11-501901). 1 µmol each of N,N'-diacetylated hydrazino derivative of the respective oligosaccharides was completely methylated according to the method of Anumula et al. (supra). The resulting completely methylated N,N'-diacetylated hydrazino oligosaccharide derivative was placed in a glass test tube and dried. 500 µl of 5% hydrochloric acid-methanol (Nacalai Tesque) was added to the test tube. The tube was sealed and heated at 90° C. for 4 hours. The tube was opened, and the sample was dried using a centrifugation concentrator to obtain a cleavage product. 300 µl of a 2:1 mixture of pyridine and acetic anhydride was added to the residue obtained after methanolysis. After adequately stirring, the mixture was incubated at 37° C. for 2 hours. The sample was dried using a centrifugation concentrator. The residue was dissolved by adding 1000 µl of an acetonitrile aqueous solution thereto and each PMHAA was recovered.

GC/MS Analysis

1 µl of each PMHAA solution in acetonitrile (corresponding to 1 nmol of the starting material) was analyzed by subjecting it to GC/MS by splitless injection. GC/MS analysis was carried out as follows:
System: GCQ (Finnigan MAT)
Column: DB-5 (5% diphenyl-95% dimethyl polysiloxane, 0.25 mm i.d.×30 m, 0.25 micrometer film thickness) (J & W Scientific)
Carrier: Herium (40 cm/sec)
Ionization: CI (Isobutane)
Injector temperature: 300° C.
Column initial temperature: 90° C.
Time program: 90° C. for 2 min, 90° C.—(24° C./min)—210° C., and 210° C.—(4° C./min)—300° C.
Injection: 1 microliter (splitless injection)

Plural peaks were observed for each PMHAA sample upon GC/MS analysis. The peaks for PMHAAs were identified based on positive molecular ions found in the respective chemical ionization mass spectra.

The results confirmed the following: 4-O-acetyl-1-deoxy-2,3,5,6-O-tetramethyl-1-(N,N'-diacetyl-N'-methylhydrazino)-D-glucitol resulted from lactose; 2-O-acetyl-1-deoxy-3,4,5,6-O-tetramethyl-1-(N,N'-diacetyl-N'-methylhydrazino)-D-mannitol resulted from mannobiose; 3,6-O-diacetyl-1-deoxy-2,4,5-O-trimethyl-1-(N,N'-diacetyl-N'-methylhydrazino)-D-mannitol resulted from mannotriose; and 4-O-acetyl-1,2-dideoxy-3,5,6-O-trimethyl-2-(N-methylacetoamido)-1-(N,N'-diacetyl-N'-methylhydrazino)-D-glucitol resulted from N-acetyl lactosamine.

Upon GC/MS analysis of 4-O-acetyl-1-deoxy-2,3,5,6-O-tetramethyl-1-(N,N'-diacetyl-N'-methylhydrazino)-D-glucitol obtained from lactose, a positive molecular ion peak ([M+H]$^+$) at m/z=393 was detected in the chemical ionization mass spectrum for the peak at 11.4 minutes. Upon GC/MS analysis of 2-O-acetyl-1-deoxy-3,4,5,6-O-tetramethyl-1-(N,N'-diacetyl-N'-methylhydrazino)-D-mannitol obtained from mannobiose, a positive molecular ion peak ([M+H]$^+$) at m/z=393 was detected in the chemical ionization mass spectrum for the peak at 11.1 minutes. Upon GC/MS analysis of 3,6-O-diacetyl-1-deoxy-2,4,5-O-trimethyl-1-(N,N'-diacetyl-N'-methylhydrazino)-D-mannitol obtained from mannotriose, a positive molecular ion peak ([M+H]$^+$) at m/z=421 was detected in the chemical ionization mass spectrum for the peak at 13.1 minutes. Upon GC/MS analysis of 4-O-acetyl-1,2-dideoxy-3,5,6-O-trimethyl-2-(N-methylacetoamido)-1-(N,N'-diacetyl-N'-methylhydrazino)-D-glucitol obtained from N-acetyl lactosamine, a positive molecular ion peak ([M+H]$^+$) at m/z=434 was detected in the chemical ionization mass spectrum for the peak at 14.5 minutes.

Example 5
Preparation and Methylation Analysis of Ultraviolet Absorbance-Labeled Hydrazide Derivative 25 µl of a solution containing 25 µmol of benzoylhydrazine (Tokyo Kasei Kogyo) in dimethyl sulfoxide (DMSO) was added to 5 µmol of glucose (Nacalai Tesque), sophorose (Glcβ1-2Glc, Sigma), laminaribiose (Glcβ1-3Glc, Seikagaku Corporation), maltose (Glcα1-4Glc, Kanto Kagaku) or isomaltose (Glcα1-6Glc, Seikagaku Corporation) which had been dried adequately, and the saccharide was fully dissolved by sonication. 2.5 µl of acetic acid was added thereto and the mixture was stirred adequately. The reaction mixture was then heated at 90° C. for 1 hour. The reaction mixture was dried using a centrifugation concentrator. 50 µl of a solution containing 2.5 M borane-dimethylamine complex and 30% acetic acid in DMSO was added to the residue, and the residue was fully dissolved by sonication. The mixture was then incubated at 37° C. for 16 hours. The reaction mixture was dried using a centrifugation concentrator. Addition of acetonitrile and drying were repeated. The residue was dissolved in 100 µl of water. Excess reagents were removed by three rounds of extraction with 300 µl of water-saturated ethyl acetate. The method as described in WO 96/17824 (JP-A 11-501901) was used for carrying out N-acetylation. After desalting using Dowex 50W-X8 (Muromachi Kagaku) followed by further purification using HPLC, N-acetylated benzoylhydrazine saccharide derivatives were obtained. HPLC was carried out as follows:
Pump: LC6A (Shimadzu)
Column: Asahipak NH2P-50 (4.6 mm i.d.×250 mm) (Showa Denko)
Solvent A: Acetonitrile/water, 95:5
Solvent B: Acetonitrile/water, 1:1
Flow rate: 1 ml/min
Temperature: 40° C.
Gradient: 0–100% Solvent B in 30 min
Detection: Absorbance at 270 nm 1 µmol each of the N-acetylated benzoylhydrazine saccharide derivatives was completely methylated according to the method of Anumula et al. (supra). A ½₀ amount of the resulting completely methylated N-acetylated benzoylhydrazine saccharide derivative was placed in a glass test tube and dried. 100 µl of a 80% acetic acid aqueous solution containing 0.5 M hydrochloric acid was added to the test tube. The tube was sealed and heated at 100° C. for 6 hours. The tube was opened, and the sample was dried using a centrifugation concentrator to obtain a cleavage product. 200 µl of a 2:1 mixture of pyridine and acetic anhydride was added to the residue. After adequately stirring, the mixture was incubated at 37° C. for 16 hours. The sample was dried using a centrifugation concentrator. The residue was dissolved by adding 100 µl of an acetonitrile aqueous solution thereto to recover PMHAA.

GC/MS Analysis

1 µl of the PMHAA solution in acetonitrile (corresponding to 1 nmol of the starting material) was analyzed by subjecting it to GC/MS by splitless injection. GC/MS analysis was carried out as follows:
System: GCQ (Finnigan MAT)
Column: DB-5 (5% diphenyl-95% dimethyl polysiloxane, 0.25 mm i.d.×30 m, 0.25 micrometer film thickness) (J & W Scientific)
Carrier: Herium (40 cm/sec)
Ionization: CI (Isobutane)
Injector temperature: 300° C.
Column initial temperature: 90° C.
Time program: 90° C. for 2 min, 90° C.—(24° C./min)—210° C., and 210° C.—(12° C./min)—300° C.
Injection: 1 microliter (splitless injection)

Plural peaks were observed in a total mass chromatogram for each PMHAA. A single peak was observed at 9.2 minutes in a single mass chromatogram for a positive molecular ion ([M+H]$^+$) at m/z=393 for the expected PMHAA for the sample from N-acetylated benzoylhydrazine glucose. Single peaks were observed at 9.4 minutes, 9.5 minutes, 9.6 minutes and 10.2 minutes in single mass chromatograms for positive molecular ions ([M+H]$^+$) at m/z=393 for the expected PMHAAs for the remaining four samples from N-acetylated benzoylhydrazine sophorose, N-acetylated benzoylhydrazine laminaribiose, N-acetylated benzoylhydrazine maltose and N-acetylated benzoylhydrazine isomaltose, respectively. The mass spectra for PMHAA peaks for respective samples were clearly different each other among the samples. Accordingly, it was demonstrated that the position of an acetyl group can be identified based on the difference in a mass spectrum or a fragmentation pattern of PMHAA.

Example 6
Preparation and Stability Test of N-acetylated Labeled Hydrazino Derivative 100 μl of a solution containing 100 μmol of benzoylhydrazine (Tokyo Kasei Kogyo) in DMSO was added to 50 μmol of N-acetyl lactosamine (Seikagaku Corporation, hereinafter referred to as LN) which had been dried adequately, and the saccharide was fully dissolved by sonication. 80 μl of DMSO and 20 μl of acetic acid were added thereto and the mixture was stirred adequately. The reaction mixture was then heated at 90° C. for 1 hour. The reaction mixture was dried using a centrifugation concentrator while heating. 500 μl of a 25% acetonitrile aqueous solution containing 2 M sodium boron hydride (Nacalai Tesque) was added to the residue, and the mixture was adequately stirred and allowed to stand at room temperature overnight. 500 μl of pure water was added to the reaction mixture. The reaction mixture was then neutralized by adding acetic acid dropwise to make the pH of the solution to about 5. 800 μl of the neutralized solution was placed in a test tube. 1 ml of pure water was further added thereto for dilution. The method as described in WO 96/17824 (JP-A 11-501901) was used for carrying out N-acetylation. After desalting using Dowex 50W-X8 (Muromachi Kagaku) followed by further purification using HPLC, an N-acetylation product of a benzoylhydrazine derivative of LN (hereinafter referred to as LN benzoylhydrazine derivative) was obtained. On the other hand, an LN benzoylhydrazine derivative was prepared without N-acetylation. 100 μl of a solution containing 100 μmol of benzoylhydrazine (Tokyo Kasei Kogyo) in DMSO was added to 50 μmol of LN (Seikagaku Corporation) which had been dried adequately, and the saccharide was fully dissolved by sonication. 80 μl of DMSO and 20 μl of acetic acid were added thereto and the mixture was stirred adequately. The reaction mixture was then heated at 90° C. for 1 hour. The reaction mixture was dried using a centrifugation concentrator while heating. 500 μl of a 25% acetonitrile aqueous solution containing 2 M sodium boron hydride was added to the residue, and the mixture was adequately stirred and allowed to stand at room temperature overnight. 500 μl of pure water was added to the reaction mixture. The reaction mixture was then neutralized by adding acetic acid dropwise to make the pH of the solution to about 5. 200 μl of the neutralized reaction mixture was dried using a centrifugation concentrator and purified using HPLC to obtain an LN benzoylhydrazine derivative. HPLC was carried out as follows:
Pump: LC6A (Shimadzu)
Column: Asahipak NH2P-50 (4.6 mm i.d.×250 mm) (Showa Denko)
Solvent A: Acetonitrile/water, 95:5
Solvent B: Acetonitrile/water, 1:1
Flow rate: 1 ml/min
Temperature: 40° C.
Gradient: 0–100% Solvent B in 30 min
Detection: Absorbance at 270 nm 25 nmol each of the purified LN benzoylhydrazine derivative and the N-acetylation product thereof was dissolved in 5 μl of a 10, 30 or 50% acetic acid solution in DMSO. The solution was incubated at 37° C. overnight. The solution was dried and re-dissolved in 5 μl of pure water. 0.5 μl of the solution was spotted onto HPTLC (Merck) and developed using a 80% acetonitrile aqueous solution. Neutral sugars were detected according to the orcinol-sulfuric acid method.

Results of thin-layer chromatography are shown in FIG. 1. The following samples were developed in the lanes in FIG. 1: lane 1: the untreated LN benzoylhydrazine derivative; lane 2: the LN benzoylhydrazine derivative incubated in a solution containing 10% acetic acid in DMSO; lane 3: the LN benzoylhydrazine derivative incubated in a solution containing 30% acetic acid in DMSO; lane 4: the LN benzoylhydrazine derivative incubated in a solution containing 50% acetic acid in DMSO; lane 5: the untreated N-acetylated LN benzoylhydrazine derivative; lane 6: the N-acetylated LN benzoylhydrazine derivative incubated in a solution containing 10% acetic acid in DMSO; lane 7: the N-acetylated LN benzoylhydrazine derivative incubated in a solution containing 30% acetic acid in DMSO; and lane 8: the N-acetylated LN benzoylhydrazine derivative incubated in a solution containing 50% acetic acid in DMSO.

The LN benzoylhydrazine derivative was converted under acidic conditions into a substance that exhibited lower mobility on TLC, whereas no change was observed for the N-acetylated LN benzoylhydrazine derivative. Thus, the chemical stability of the N-acetylated benzoylhydrazine derivative was demonstrated.

INDUSTRIAL APPLICABILITY

The present invention provides a means that enables determination of the type and the substitution position of a monosaccharide at a reducing end of a saccharide even if it is not isolated.

What is claimed is:

1. A method for determining a position of binding of a monosaccharide at a reducing end to a neighboring monosaccharide, the method comprising at least:

(a) reacting a saccharide having a reducing end with a hydrazine of formula (I) to produce a hydrazone:

$$NH_2-NR^1(R^2) \qquad (I)$$

wherein $R^1$ is a group other than hydrogen that has a detectable label and/or an immobilization support as its portion or can bind to a detectable label and/or an immobilization support; the bond between $R^1$ and N is a bond that is cleavable by a reaction that can cleave a glycosidic linkage; and $R^2$ is hydrogen or an alkyl group containing 1–8 carbon atoms;

(b) reducing the hydrazone obtained in step (a) to a hydrazino derivative;

(c) N-acetylating the hydrazino derivative obtained in step (b);

(d) methylating a hydroxy group of the hydrazino derivative obtained in step (c);

(e) cleaving the hydrazino derivative obtained in step (d) by the reaction that can cleave a glycosidic linkage to obtain a hydrazino monosaccharide derivative;

(f) completely acetylating the hydrazino monosaccharide derivative obtained in step (e); and (g) identifying the acetylated hydroxyl group in the completely acetylated hydrazino monosaccharide derivative obtained in step (d), and determining a position of binding of a monosaccharide at a reducing end to a neighboring monosaccharide.

2. The method according to claim 1, wherein the identification in step (e) is carried out using gas chromatography/mass spectrometry CGC/MS).